United States Patent [19]
Keim

[11] Patent Number: 5,341,516
[45] Date of Patent: Aug. 30, 1994

[54] GOGGLE SUPPORT SYSTEM

[76] Inventor: Eric Keim, 2914 Mountain View Dr., Laguna Beach, Calif. 92651

[21] Appl. No.: 994,929

[22] Filed: Dec. 22, 1992

[51] Int. Cl.[5] .............................. A61F 9/02; A42B 3/00
[52] U.S. Cl. ................................. 2/452; 2/5; 2/424
[58] Field of Search ............... 2/5, 10, 424, 426, 452, 2/DIG. 6, 338, 265, 422; 24/200, 306

[56] References Cited

U.S. PATENT DOCUMENTS

| | | | |
|---|---|---|---|
| 3,373,444 | 3/1968 | Militello | 2/10 |
| 4,112,521 | 9/1978 | Uke | 2/452 |
| 4,193,133 | 3/1980 | Laibach et al. | 2/10 |
| 4,259,747 | 4/1981 | Taesler et al. | 2/423 |
| 4,276,657 | 7/1981 | Montesi | 2/10 |
| 4,619,003 | 10/1986 | Asbury | 2/5 |
| 4,686,712 | 8/1987 | Spiva | 2/10 |
| 4,796,308 | 1/1989 | Bourgeois | 2/10 |
| 4,847,920 | 7/1989 | Aileo et al. | 2/10 |
| 5,107,543 | 4/1992 | Hansen | 2/426 |

FOREIGN PATENT DOCUMENTS 735281  5/1943  Fed. Rep. of Germany .......... 2/452

Primary Examiner—Clifford C. Crowder
Assistant Examiner—Michael A. Neas
Attorney, Agent, or Firm—Hawes & Fischer

[57] ABSTRACT

The goggle system of the present invention has a first embodiment which extends continuously between the goggle fittings and includes a first end which is webbing reinforced, threadedly attached through a standard tension lock buckle in a position to be drawn rearwardly along the side of the head of the user to tighten. Spaced from the fold, a patch of hook-like members is sewn to the strap in a position oriented away from the user's head to accept attachment of the reinforced end.

The second embodiment includes a goggle strap which is not continuous, and is terminated at a patch of hook-like members. Between the patch of hook-like members and the tension buckle is a grommet sized to interfit with fittings on the side of the helmet.

10 Claims, 3 Drawing Sheets

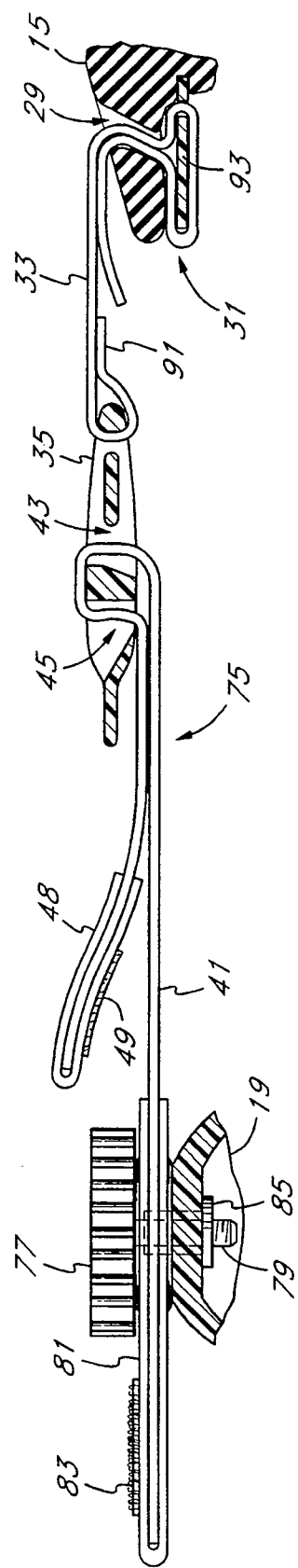

GOGGLE SUPPORT SYSTEM

FIELD OF THE INVENTION

The present invention relates to the field of systems for the support and utilization of goggles in a variety of different situations. More specifically, the present invention relates to a system for efficient utilization of goggles in the fire fighting environment, both with and without the use of fittings on a fire fighting helmet.

BACKGROUND OF THE INVENTION

Early fire helmets were designed without goggles or face shields. These helmets provided no protection for the eyes or face from the hazardous environments that fire fighters face. However, modern fire helmets incorporate the use of a face shield, and the inclusion of a shield was mandated by the National Fire Protection Association, NFPA, 1972. These face shields are generally sheets of material which extend curvingly about the front portion of a helmet. The shields are usually curved about a vertical axis, and are attached to the helmet at their upper corners which are almost parallel to each other due to the shield's curvature. They are usually pivotable with respect to the helmet and can be raised and lowered much like the visor on a suit of armor is raised and lowered.

These face shields unfortunately have many design flaws, including lack of protection for eyes from objects or particles that come from an upward deflection under the lower edge of the shield or from a side upward deflection around the outer vertical edge of the shield. The shields also have a high tendency to fog due to the distance of the shield from the face, and in conjunction with the seal at the top with the helmet which reduces upward ventilation of both exhaled air and evaporation of sweat from the face.

Face shields are stored while still attached to the top of the helmet. This mounting, together with their large size, causes face shields to receive damage, such as scratches and abrasions, rendering face shields virtually useless to see through over even a short period of time. When in service, the shields come into contact with smoke residue and heat. These conditions cause the shields to degrade even more rapidly as the scratches trap the smoke residue and bake it into the exposed pores of the shield.

The shields, which are typically made of plastic, are extremely difficult to clean. Many solvents which would be effective in removing the smoke residue would also cause dissolution of the plastic. Further, as time elapses, the collection of scratches and smoke residue seriously impair the fire fighter's ability to see. The shields typically lie a few inches in front of the fire fighter's eyes. It is much more difficult to discount distortions in the visual field when they occur this far from the eyes. There is a tendency to continually confuse obstructions on the shield with objects in the visual plane.

Such confusion from distortions on the shield occurs not only over time, but can occur with a new shield upon its first use. This is due to the conditions under which fires are battled, in which a shield may become obstructed with smoke residue and dirt and water even if it is in an otherwise unscratched state. In the heat of the moment when fighting a fire, the fire fighter's only quick recourse to a dirty shield is to rub away the dirt and debris with the hands or gloves. Due to the size of the shield, this will result in streaks and larger distortions. Further attempts to remove these streaks and larger distortions will only cost the fire fighter more time, time being a premium commodity during the fighting of a fire.

Further, due to the shield's distance from both the eyes and face, smoke residue, dirt and water can collect on the shield from the inside as well as the outside to compound the obstruction of the fire fighter's vision. Attempts to quickly, with the hands or gloves, wipe clean a surface having two obstructed sides are nearly impossible. Further, the face shields allow smoke to come into direct contact with the fire fighter's eyes.

Face shields also increase the overall weight of the helmet by more than fourteen ounces, and add mass forward of the helmet resulting in a forward, downward bending moment causing increased neck strain and fatigue on the wearer of the helmet. Face shield mounting hardware has a tendency to loosen with use and make the shield hang halfway down, obstructing sight with the bottom edge of the shield most prominent in the field of view.

Some of the shields currently in use are, for example, the S-601 Polycarbonate lens, the Hi-Pivot, S-901 Tuff-shield, and the S-10 Bourke safety eye shield, all made by Cairns and Brothers. Others include the catalog No. 50110 four inch polycarbonate face shield and the No.50112 polycarbonate face shield manufactured by Cascade Fire Equipment Co. These designations may be trademarks of their respective manufacturers.

The use of goggles can assist in the elimination of some of the shortcomings of the shield. Goggles are currently available in several forms from the manufacturers. They may be purchased with a standard width $\frac{1}{2}$ inch wide rubber band which may be pre-adjusted before wear or before storage. Some of the goggle straps available include neoprene rubber and several are made by Cascade Fire Equipment Co. The pre-adjustment causes the band to either be adjusted to fit the helmet in the storage position, or to fit the wearer without the helmet. Adjustment can be a significant problem, especially with rubber or elastic since the loose end must be "picked" out of the strap keeper in order to make the adjustment. Unfortunately, the goggles cannot be adjusted on the helmet and later worn on the face without hanging loosely on the face. The narrow strap also becomes uncomfortable if worn for too long of a period of time.

General problems with ordinary rubber strapping includes its lack of quick adjustability from face to helmet, easy breakage of the thin rubber, the susceptibility of the rubber to melting, and the fact that it is not securable to the helmet.

Goggle manufacturers commonly supply consumers with ordinary, somewhat shorter straps for wearing the goggles directly, without a helmet. Such straps can sometimes be used to hold goggles to helmets. Originally, these straps were designed to fit the head of the wearer without a helmet. They were not designed to function both on the helmet and later on the face. Previous goggle retainers are unable to adequately function for that purpose.

Later, other types of retainers were created for helmet use. One company known both as "Mine Safety" and "M.S.A." has manufactured a hard plastic band that mounts to the rear edge of the helmet and secures with a rubber tube around the front of the helmet. This plastic tube then contains an elastic string which secures to the goggles. This system is effective for helmets with a brim, but the elastic string tends to experience stretch failure rather rapidly, and becomes loose while in the donned position, requiring constant re-tying until no elasticity remains in the string. Other problems include the inability of the "Mine Safety" system to fit over new NFPA required edge protection, the fact that all of the components used in this system can melt or be damaged by heat, and that the system is designed to be used only with helmets.

Another goggle maker has a retainer consisting of a buckle to adjust the goggles. This buckle is mountable to only their brand goggle, and works only with the ½ inch rubber band. This buckle is specifically designed for that use. It is difficult to use with gloves and can be difficult to doff.

What is therefore needed is a system for the protection of fire fighter's eyes from heat, smoke and debris, which is easily managed and can be wiped adequately clean in a moment if obstructed. It should be amenable to being worn either with or without a helmet, and should be adjustable by the wearer rapidly and when in place on either a helmet or the wearer's head. The system should employ support structures which will always work. If the design contains elastic, it should work even if the elastic wears out. The system should be easy to use with gloved hands, and during fire fighting operations.

SUMMARY OF THE INVENTION

The goggle system of the present invention consists of a nylon or Nomex/PBI elastic material, and has two embodiments. The first embodiment extends continuously between the goggle fittings. The material includes a first end which is covered and sewed with a folded length of nylon webbing. The nylon webbing supports a sewn felt-like member patch. The end is threadedly attached through a standard tension lock buckle in a position to be drawn rearwardly along the side of the head of the user to tighten. About four inches in length along the main body of the strap from the nylon webbing reinforcement, a patch of hook-like members is sewn to the strap in a position oriented away from the user's head. Once the fold end is pulled rearward to adjust the strap, the felt-like members on the fold can be pressed to the hook-like members of the patch on the main body of the strap. Further, the center of the strap, where it crosses the back of the user's head, may include a long patch of felt-like members which may be used in conjunction with a matching strip of hook-like members affixed to the rear of a helmet.

The second embodiment differs from the first embodiment in that the goggle system strap is not continuous, and is terminated a short distance from the patch of hook-like members. A grommet is located between the tension lock buckle and the patch of hook-like members and closer to the patch of hook-like member. The grommet is sized to interfit with a fitting on the helmet. This fitting is typically a metallic threaded aperture mounted into the side of a helmet and is usually engaged with a threaded shaft mounted with a large knob for thumb and forefinger operation.

BRIEF DESCRIPTION OF THE DRAWINGS

FIG. 5 is a cross sectional view of the goggle strap taken along line 5—5 of FIG. 3; and FIG. 6 is a cross sectional view of the goggle strap taken along line 6—6 of FIG. 4.

DETAILED DESCRIPTION OF THE PREFERRED EMBODIMENT

Figure 1:
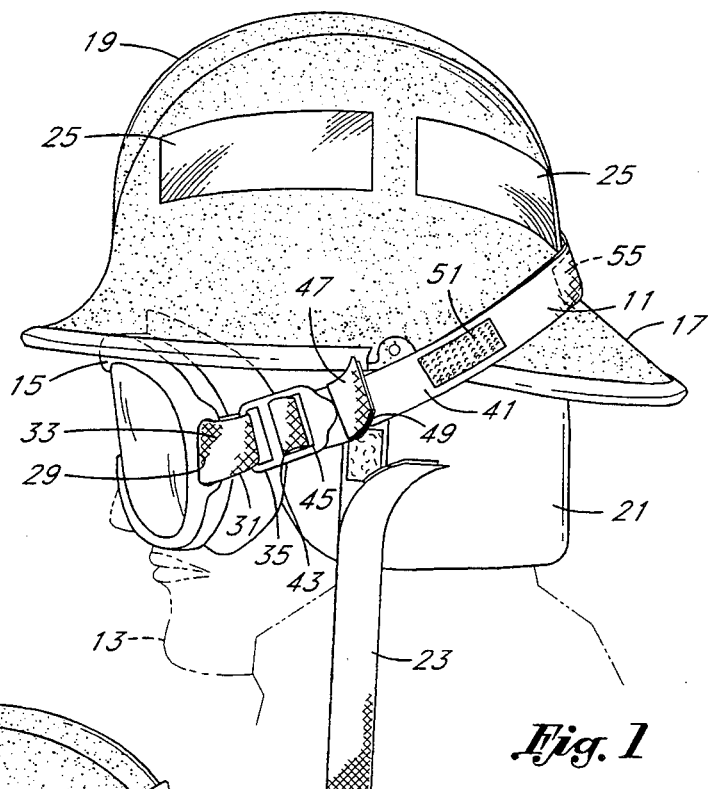
FIG. 1 is a left side view of a fire fighter with helmet and illustrating a first embodiment of the goggle strap of the present invention.

The description and operation of the invention will begin with reference to a first embodiment shown in FIG. 1. This first embodiment is a goggle system 11 which is shown attached to the face of a fire fighter 13 shown in phantom. The goggle system 11 extends from one side of a pair of goggles 15, upwardly around the rear lip 17 of a helmet 19.

The helmet shown in FIG. 1 is also fitted with a rearwardly located neck flap 21 and a commonly available chin strap 23 which is shown suspended in a vertical, unattached position. Helmet 19 also has a pair of reflectors 25 attached along its top surface.

The goggles 15 have side apertures 29 in side buckle structures 31 through which is threaded a forestrap 33 of the goggle system 11. Forestrap 33 is preferably made of nylon webbing and is preferably about three-fourths of an inch wide. It is understood that some goggles 15 may have integral apertures 29 and buckle structures 31, formed apertures 29 and buckle structures 31, or attached apertures 29 and buckle structures 31. In the example of FIG. 1, the fore strap 33 is a simple length of material preferably having a first end whose edge is slightly angled, and a second end sewn into a loop which is looped about one side of a standard tension lock buckle 35.

The angled end of the fore strap 33 is then threaded through the buckle structures 31 of the goggles 15. This is typically accomplished by threading the fore strap 33 through an aperture 29, then backwards about another structure and then back through the aperture 29. Many such methods are known to attach the free end of a strap to a piece of equipment such as a pair of goggles 15.

Referring again to the standard tension lock buckle 35, a main strap 41 portion of the goggle system 11 is threaded through a first main aperture 43 and back through a second main aperture 45. Main strap 41 is preferably made of nylon elastic material having a degree of stretch, and is typically about twenty five inches long. The preferable width for main strap 41 is about one inch wide. The main strap 41 portion of the goggle system 11 has an end 47 which has a length of nylon webbing 48 folded in a U-shape about its end. The nylon webbing 48, shown having a darkened edge due to its increased thickness, is sewn with a patch 49 containing an array of felt-like members, more commonly known and sold under the name VELCRO. Note that the felt-like surface is arranged to face the portion of the main strap 41 portion in a flat position as it extends from standard tension lock buckle 35.

Rearwardly along main strap 41 portion is a patch 51 of hook-like members capable of interlocking with the felt-like members of patch 49. In this manner, the fire fighter 13 can reach the end 47 of the main strap 41, pull it rearwardly to tighten the main strap 41, and with slight pressure press the felt-like members of patch 49 against the hook-like members of patch 51 to secure the end 47 of main strap 41 and to prevent it from dangling to the side of the helmet 19 in an annoying manner.

For re-adjustment, the fire fighter 13 can reach the end 47 of the main strap 41, lift it with his thumb, even if gloved, and pull it further rearwardly, or simply dislodge it from its secure position. The fire fighter can then grasp the standard tension lock buckle 35, and turn and pull it forward to loosen the goggle system 11.

At the rear center portion of the goggle system 11, and shown in phantom, is an optional second velcro-type connection. The center of the goggle system 11 may have a patch 55 of felt-like members facing the outer surface of the helmet 19. Helmet 19 can have a patch (not specifically shown in FIG. 1) of hook-like members attached to the helmet 19, especially near the junction where the lip 17 meets the rear portion of the helmet 19. Such attachment may be accomplished by an adhesive strip, by gluing, or by the riveting of a preformed plate containing hook-like members. This second velcro-type connection would serve to further secure the goggle system 11 with respect to the helmet 19.

Figure 2:
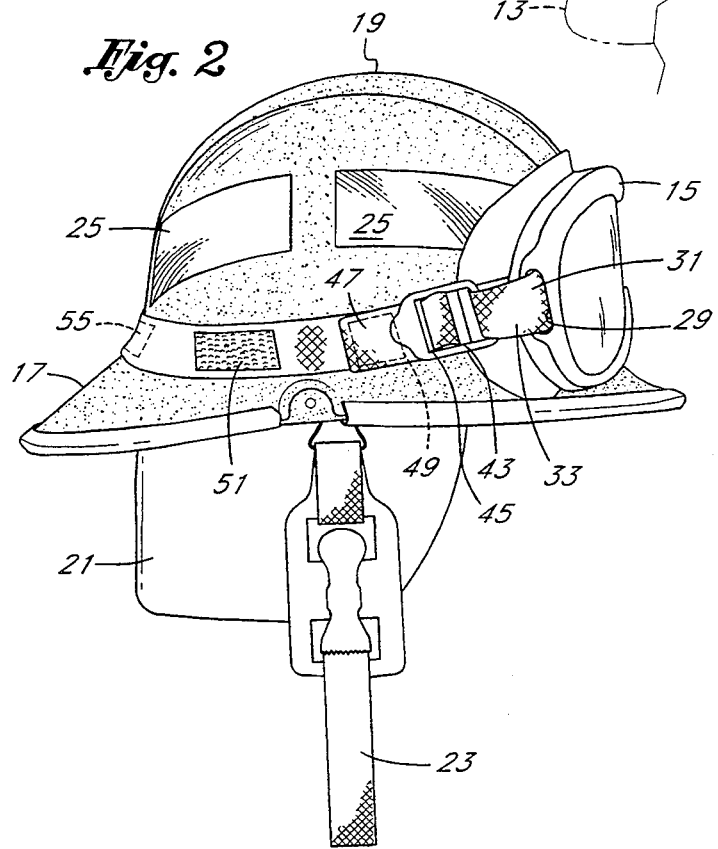
FIG. 2 is a right side view of the helmet and goggle strap illustrated in FIG. 1.

Referring to FIG. 2, the helmet 19 of FIG. 1 is shown with the goggles 15 in the rest position atop the helmet 19. Although the fire fighter 13 is not shown in FIG. 2, the rest position for the goggles 15 may be had whether or not the helmet 19 is being worn. Note how the second velcro-type connection including patch 55 assists in holding the goggle system 11 in position on the helmet 19 even though the surfaces of helmet 19 surrounded by the goggles 15 and goggle system 11 are upwardly swept surfaces. Goggle system 11 provides great ease in moving the goggles 15 from the rest position shown in FIG. 2 to the worn position of FIG. 1 and back again, even when the fire fighter 13 is wearing gloves. In FIG. 2, patch 49 is shown in phantom.

Figure 3:
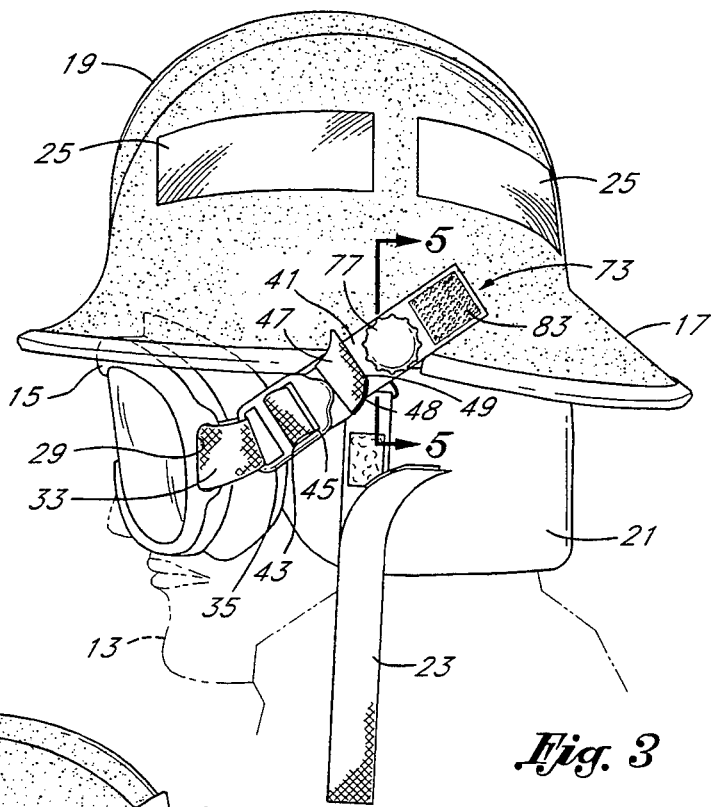
FIG. 3 is a left side view of a fire fighter with helmet and illustrating a second embodiment of the goggle strap of the present invention attached to the helmet.
Figure 4:
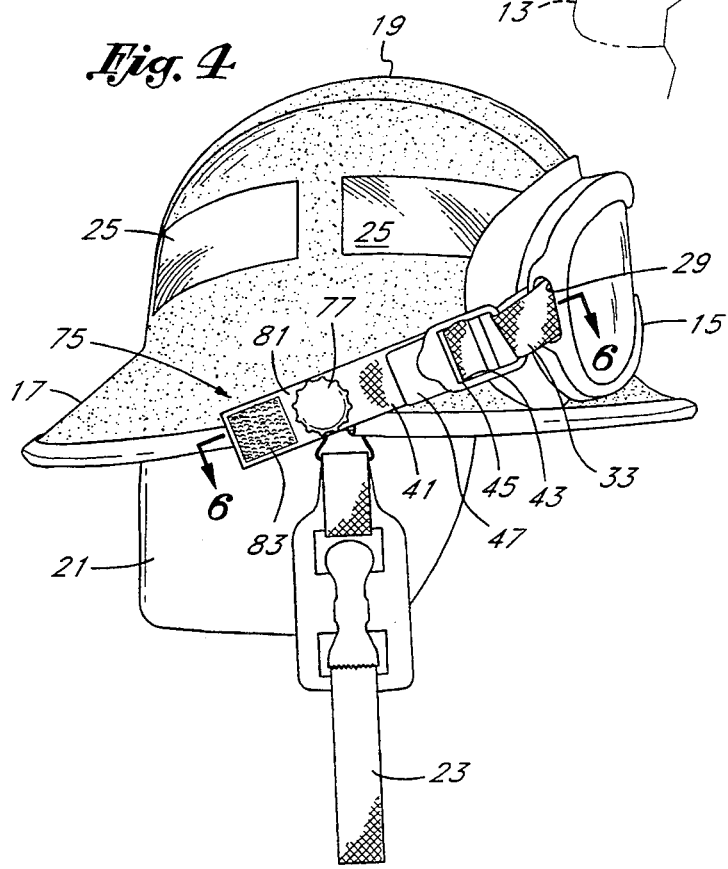
FIG. 4 is a right side view of the helmet and goggle strap illustrated in FIG. 1.

Referring to FIG. 3, a second embodiment of the goggle system of the present invention is shown in a manner similar to that as shown in FIG. 1. In FIGS. 3 and 4, the numbering will be the same except where the structure differs. Those items identified in FIGS. 1 and 2 will not be further identified except as necessary to describe the second embodiment. The second embodiment of the goggle system of the present invention differs from the first principally in that it occurs in two sections rather than one continuous length extending completely about the users helmet 19 or head. The two separate sections attach individually at their ends to the helmet 19 as will be shown.

The second embodiment of the goggle system of the present invention will be referred to as goggle system 71. It consists of a left side strap 73, which is shown in FIG. 3, and a right side strap 75 which is shown in FIG. 4. Referring to FIG. 3, the left side strap 73, as it engages goggles 15 and extends rearward, is identical to the structure shown for the left side of goggle system 11, including the structures of forestrap 33, standard tension lock buckle 35, main strap 41 portion, main aperture 43, second main aperture 45, end 47, length of nylon webbing 48, and patch 49.

However, slightly behind the end 47 of the main strap 41 portion of the left side strap 73 is a thumb wheel 77 for a thumb screw 79 (shown in FIG. 5). The thumb wheel 77 enables easy attachment of the left side strap 73 to the helmet 19, by having the thumb screw 79 extend through the side strap 73 to attach it to the side of the helmet, yet enable the left side strap 73 to pivot about the axis of the thumb wheel 77 and thumb screw 79.

The rearward portion of the left side strap 73, from a position just in front of the thumb wheel 77, to its rearward end contains a U-shaped length of nylon webbing 81 sandwiching the end of left side strap 73. This provides reinforcement which will be necessary to provide the reinforcing structure necessary to withstand forces transmitted through the thumb screw 79, as will be shown.

To the rear of the thumb wheel 77 and at the rearward most end of the left side strap 73 is a patch 83 of hook-like members capable of interlocking with the felt-like members of patch 49. The patch 83 is carried by the nylon webbing 81 which is sewn to the end of left side strap 73. In a manner similar to that described for the first embodiment, the fire fighter 13 can reach the end 47 of the main strap 41, pull it rearwardly to tighten the main strap 41, pull it past and across the thumb wheel 77 and with slight pressure press the felt-like members of patch 49 against the hook-like members of patch 83 to secure the end 47 of main strap 41 and to prevent it from dangling to the side of the helmet 19 in an annoying manner. The views of FIGS. 3 and 4 do not show the end 47 of main strap 41 in this engaged position, in order that the thumb wheel 77 may be fully shown.

Referring to FIG. 4, the details of the right side strap 75 are shown. In FIG. 4, as was the case for FIG. 2, helmet 19 is shown with the goggles 15 in the rest position atop the helmet 19. Again, although the fire fighter 13 is not shown in FIG. 4, the rest position for the goggles 15 may be had whether or not the helmet 19 is being worn. Note the pivoting action about the thumb wheel 77.

In this configuration of the second embodiment the goggle system 71 is in secure position with respect to the helmet 19 and cannot fall off. Although this configuration does not provide for removal of the goggles 15 to be worn about the head independent of the presence of the helmet 19, this configuration provides a superior stability for the goggles 15 when the helmet is in use. The thumb wheel 77 also provides ease in attaching and removing the goggles 15 to and from the helmet 19.

Referring to FIG. 5, the sectional view taken along section 5—5 of FIG. 3 shows the details of attachment of the left side strap 73 to the helmet 19. The thumb screw 79 is shown extending from the thumb wheel 77, and into a nut 85. Nut 85 may be press fit into the side of helmet 19, or glued, or held in by the axial force of the thumb screw 79. The area surrounding the portion of the main strap 41 reinforced by the nylon webbing 81 contains a washer grommet 89. It is preferable to use a #2 size brass washer grommet 89, such as the type commercially available by Lord & Hodges Company. Both the main strap 41 and the nylon webbing 81 are clearly shown being partially encased on both sides by the washer grommet 89.

Referring to FIG. 6, the sectional view taken along section 6—6 of FIG. 4 shows further details of attachment of the right side strap 75 to the helmet 19 and goggles 15, as well as a detailed view of the layers making up the right side strap 75. Right side strap 75 is symmetrically identical to left side strap 73. The thumb screw 79 is again shown extending from the thumb wheel 77, and into a nut 85. Also shown clearly is the manner in which the nylon webbing 81 sandwiches the end of right side strap 75. Also shown clearly is the manner in which the nylon webbing 48 sandwiches the end 47 of right side strap 75, and the location of patch 49 and its felt like members on the nylon webbing 48.

Further details of the threading of the main strap 41 portion of the right side strap 75 through the standard tension lock buckle 35 are shown including the main aperture 43 and second main aperture 45 through which the main strap 41 is threaded. Also shown are the details of the standard tension lock buckle 35's attachment to the forestrap 33, including a sewn area 91 of the forestrap 33, permanently securing it to the standard tension lock buckle 35.

At the forward most end of right side strap 75 are the details of the connection to the edge of the goggles 15 including the side apertures 29 and buckle structures 31. Buckle structures 31 include an inner member 93 which has a width wider than the aperture 29. This provides a close secure fit for the forestrap 33 to secure the right side strap 75 to the goggles 15.

While the present invention has been described in terms of a goggle support system for a fire fighter's helmet, one skilled in the art will realize that the structure and techniques of the present invention can be applied to many appliances. The present invention may be applied in any situation where quick, easy and adjustable support is sought.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed is:

1. A side strap for a goggle support system for securing goggles comprising:
   a tension lock buckle;
   a forestrap permanently attached to said tension lock buckle;
   a main strap portion having a first end extending through said first tension lock buckle and a second end;
   a patch of felt-like material attached to said first end of said main strap;
   a patch of hook-like material attached adjacent to said second end of said main strap portion; and
   a washer grommet supported by said main strap portion between said patch of hook-like material and said tension lock buckle.

2. The goggle support system recited in claim 1 further comprising a first U-shaped length of webbing surrounding said first end of said main strap and supporting said patch of said felt-like material.

3. The goggle support system recited in claim 2 further comprising a second U-shaped length of webbing surrounding said second end of said main strap and supporting said patch of said hook-like material.

4. The goggle support system recited in claim 2 wherein said first U-shaped length of webbing is nylon webbing.

5. The goggle support system recited in claim 3 wherein said second U-shaped length of webbing is nylon webbing.

6. The goggle support system recited in claim 1 wherein said main strap is made of nylon elastic.

7. The goggle support system recited in claim 1 wherein said forestrap is made of nylon webbing.

8. A helmet assembly including a first and a second side strap as recited in claim 1 and further comprising:
   a helmet;
   attachment means supported by said helmet for engaging said washer grommet of said first side strap on one side of said helmet and for engaging said washer grommet of said second side strap on the other side of said helmet; and
   a set of goggles engaging said first and second forestraps.

9. The helmet assembly of claim 8 wherein said attachment means further comprises:
   a first threaded washer supported by said helmet on one side of said helmet;
   a first thumbscrew threadedly engageable with said first threaded washer and through said washer grommet of said first side strap;
   a second threaded washer supported by said helmet on the other side of said helmet; and
   a second thumbscrew threadedly engageable with said second threaded washer and through said washer grommet of said second side strap.

10. The helmet assembly recited in claim 9 wherein said helmet is a fire helmet having an extended rear lip.

* * * * *